United States Patent
Liesi (10) Patent No.: US 7,659,255 B2
(45) Date of Patent: Feb. 9, 2010

(54) METHODS OF INHIBITING GLUTAMATE RECEPTORS BY ADMINISTERING THE TRIPEPTIDE KDI

(76) Inventor: Paivi Liesi, Tilkankatu 2 B 25, PI-00300 Helsinki (FI)

( * ) Notice: Subject to any disclaimer, the term of this patent is extended or adjusted under 35 U.S.C. 154(b) by 0 days.

(21) Appl. No.: 11/127,206

(22) Filed: May 12, 2005

(65) Prior Publication Data

US 2005/0288231 A1  Dec. 29, 2005

Related U.S. Application Data

(63) Continuation-in-part of application No. 10/492,850, filed as application No. PCT/FI02/00831 on Oct. 25, 2002, now abandoned.

(30) Foreign Application Priority Data

Oct. 26, 2001  (FI) .................................. 20012082

(51) Int. Cl.
*A61K 38/06* (2006.01)
*C07K 5/09* (2006.01)
(52) U.S. Cl. ..................................................... 514/18
(58) Field of Classification Search ........................ None
See application file for complete search history.

(56) References Cited

U.S. PATENT DOCUMENTS 5,721,256 A * 2/1998 Hamilton et al. ............. 514/330
5,780,090 A    7/1998 Frero et al.

FOREIGN PATENT DOCUMENTS

| DE | 200 10 297 U1 | 10/2000 |
|---|---|---|
| EP | 0 067 425 B1 | 12/1982 |
| GB | 2 284 422 A | 6/1995 |
| WO | WO 93/24155 A1 | 12/1993 |
| WO | WO 94/04560 A1 | 3/1994 |
| WO | WO 98/43686 A1 | 10/1998 |
| WO | WO 98/45325   * | 10/1998 |
| WO | WO 99/00418 A1 | 1/1999 |
| WO | WO 01/66164 A1 | 9/2001 |

OTHER PUBLICATIONS

Milman et al (1980). Acta Derma Venerol. 60, 85-87. (abstract only).*
Carney (2005). Drug Discovery Today. 10, 1268.*
Nagaratnam et al (2002). Journal of Clinical Neuroscience. 9, 473-476.*
Hanafiah et al (1989). Journal of the royal society of Medicine. 84, 48-49.*
Miura et al (2000). Experimental Neurology. 166, 115-126.*
Kawamata et al (1997). PNAS. 94, 8179-8184.*
Rogeji et al (1989). JCB. 109, 823-.*
Mercandante et al (1998). Jouranl of Pain and Symptoms Management. 16, 317-322.*
Sun et al (1993). Neuroreport. 4, 1147-1150 (abstract only).*
Hoyte et al (2004). Current Molecular Medicine. 4, 131-136.*
Mercandante et al. (1998) Journal of Pain and Symptom Management. 16, 317-322.*
Widdowson et al. (1996). Brain Research. 738, 236-242.*
Tsushida et al. (1997). J. Neurotrauma. 409-417. Abstract only.*
Hoyte et al. (2004). Current Molecular Medicine. 4, 131-136. Abstract only.*
Eric Guadagno et al., GLIA 47: pp. 138-149 (2004).
Ron Liebkind et al., Journal of Neuroscience Research 73: pp. 637-643 (2003).
Päivi Liesi et al., FEB 06825, vol. 244, No. 1, 141-148, Feb. 1989.
P. Liesi, Experientia 46 (1990).
Päivi Liesi et al., Journal of Neuroscience Research 64: pp. 144-167 (2001).
Päivi Liesi et al, Journal of Neuroscience Research 66: pp. 1047-1053 (2001).
Päivi Liesi et al., Experimental Neurology 173, pp. 31-45 (2002).
S. Murtomaki et al., Journal of Neuroscience Research 32: pp. 261-273 (1992).
Hiroshi Nishimune et al., Nature Publishing Group vol. 432, pp. 580-587, Dec. 2, 2004.
Edouard Palu et al., Journal of Neuroscience Research 69: 243-256 (2002).
Arja Pasternack et al., The Journal of Biological Chemistry, vol. 277, No. 51, pp. 49662-49667, Dec. 20, 2002.
Markus Wiksten et al., Journal of Neuroscience Research 71: pp. 338-352 (2003).
Markus Wiksten et al., Journal of Neuroscience Research 78: pp. 403-410 (2004).
Markus Wiksten et al., Journal of Neuroscience Research 78: pp. 411-419 (2004).
T. Serafini et al., Cell. Aug. 12, 1994: 78(3):409-24; PubMed Abstract ID:8062384.
P. Liesi et al., Journal of Neuroscience Research, 40:199-206 (1995).
M. Matsuzawa et al., Int. J. Devl. Neuroscience, vol. 14, No. 3, pp. 283-295, 1996.
M. Matsuzawa et al., Journal of Neuroscience Research, 53:114-124 (1998).
J. Meyerhardt et al., Cell Growth & Differentiation, vol. 10, 35-42, Jan. 1999.

* cited by examiner

*Primary Examiner*—Daniel E. Kolker
(74) *Attorney, Agent, or Firm*—Birch, Stewart, Kolasch & Birch, LLP (57) ABSTRACT

The present invention relates to a method of using biologically active peptide compounds comprising the tri-peptide motif KDI derived from the neurite outgrowth-promoting domain of laminin-1 as inhibitors of ionotropic glutamate receptors. The peptide compounds are therefore useful in methods of treating disorders responsive to the blockade of these receptors, such as Alzheimer's disease, Parkinson's disease, ALS or stroke.

14 Claims, 4 Drawing Sheets

(1 of 4 Drawing Sheet(s) Filed in Color)

METHODS OF INHIBITING GLUTAMATE RECEPTORS BY ADMINISTERING THE TRIPEPTIDE KDI

This application is a continuation-in-part of U.S. patent application Ser. No. 10/492,850, filed Apr. 16, 2004 now abandoned. Application Ser. No. 10/492,850 is the National Phase of PCT/FI2002/00831, filed Oct. 25, 2002. This application also claims priority to Application 20012082 filed in Finland on Oct. 26, 2001. The entire content of these applications are herein incorporated by reference and priority is claimed under 35 U.S.C. §§119/120.

FIELD OF THE INVENTION

The present invention relates to biologically active peptides derived from the neurite outgrowth-promoting domain of laminin-1, i.e. the γ1-chain of laminin-1. These peptides include the decapeptide RDIAEIIKDI and the truncated peptides derived therefrom comprising the biologically active domain thereof, the tri-peptide KDI. The invention is directed to a method for using biologically active peptide compounds comprising the tri-peptide motif KDI as inhibitors of ionotropic glutamate receptors. The peptide compounds are therefore useful in methods of treating disorders responsive to the blockade of these receptors.

BACKGROUND OF THE INVENTION

Laminins were identified in late 1970's as extracellular matrix proteins and components of basement membranes (Martin and Timpl, 1987) and they presently form a growing family of glycoproteins with diverse functions (Miner and Yurchenco, 2004). In recent years, the central nervous system functions of various laminins have been extensively studied, and their multiple roles in the developing and mature CNS have started to emerge (Liesi, 1990; Miners and Mercado, 2003). Numerous studies have established that laminins are widely expressed in both CNS neurons and glial cells (Wiksten et al., 2004b; Liesi et al., 2001a). One of the neurite outgrowth domains of laminin-1 has been mapped to the C-terminal decapeptide RDIAEIIKDI (Liesi et al., 1989) of the γ1-chain of laminin-1. Specifically, the γ1 laminin has been linked in promoting neurite outgrowth (Liesi et al., 2001b), neuronal migration (Liesi, 1990), and axon guidance (Wiksten et al., 2003).

Interestingly, the neurite outgrowth function of the γ1 laminin is mediated by a tri-peptide sequence KDI (Lys-Asp-Ile) located in C-terminus of the protein (Liesi et al. 2001b). This tri-peptide enhances both viability and directional neurite outgrowth of human spinal cord neurons in vitro (Wiksten et al., 2003; Liebkind et al., 2003). Recent data indicate that the KDI domain possesses dramatic neuroprotective functions in vivo: it was shown (1) to prevent kainic acid induced neuronal death in hippocampal and cortical areas of the rat (Wiksten et al., 2004b), and (2) to promote healing and functional regeneration of surgically induced spinal cord injury resulting in hind limb paralysis of adult rats (Wiksten et al., 2004a). Microscopic and molecular analyses of KDI-treated spinal cords and hippocampal tissues indicate that application of soluble KDI-peptide reduces tissue damage at the lesion site and enables both neurite outgrowth through the injured area and neuronal survival (Wiksten et al., 2004a and 2004b).

Previous studies have also shown aggregation of inwardly rectifying potassium channels (Guadagno and Moukhles, 2004) and most recently voltage gated calcium channels (Nishimune et al., 2004) by binding of a particular laminin to the channel protein, but no electrical responses were reported for this interaction.

Even though the adhesive properties have been shown to play an important role in such biological events as promotion of neurite outgrowth, neuronal migration and regeneration, the data of the present invention indicate that the neurite outgrowth KDI domain of γ1 laminin has additional diverse and important functions that shed new relevance for expression of γ1 laminin in adult CNS neurons (Wiksten et al., 2004b), and in CNS after trauma (Liesi and Kauppila, 2002) or in a neurological disorder, such as Alzheimer's disease (Murtomäki et al., 1992; Palu and Liesi, 2002).

As compelling evidence indicates that glutamate neurotoxicity (glutamate-mediated neuronal death, excitotoxicity) is a major player in all CNS trauma and neurodegenerative disorders (Mattson, 2003), most of the presently available novel drugs used clinically to treat patients with Alzheimer's disease and ALS or stroke are inhibitors of glutamate receptor function. However, many of these drugs cause significant side effects, e.g. neurotoxicity. Therefore, novel, effective, safe and non-toxic inhibitors of this receptor function are constantly needed.

SUMMARY OF THE INVENTION

In the present study we investigated the effect of γ1 laminin and its derivatives on glutamate receptor function. We found that laminin-1, and peptide derivatives of the γ1 laminin, including its previously characterized biologically active KDI domain, inhibit all known classes of ionotropic glutamate receptors. This inhibition is reversible, dose-dependent and non-competitive. Our present results elucidate a novel and unexpected function for γ1 laminin and provide one feasible mechanism for potent regenerative and neuroprotective actions of the KDI domain.

In the present invention we show that the KDI-domain of γ1 laminin is a universal and non-competitive inhibitor of both AMPA, kainate and NMDA subclasses of glutamate receptors. As glutamate neurotoxicity plays a key role in both CNS trauma and neurodegenerative disorders, this unexpected novel function of the γ1 laminin derived tri-peptide may prove clinically valuable in treatment of CNS trauma and/or disease.

Consequently, one object of the invention is a pharmaceutical composition useful for the treatment of disorders responsive to the blockade of ionotropic glutamate receptors, said composition comprising a therapeutically effective amount of a peptide compound comprising the tri-peptide KDI or a pharmaceutically acceptable salt thereof in combination with at least one pharmaceutically acceptable carrier, diluent or excipient.

Another object of the invention is a method for antagonizing the neurotoxicity mediated by ionotropic glutamate receptors in a patient, said method comprising providing to said patient a therapeutically effective amount of a pharmaceutical composition having inhibitory effect on ionotropic glutamate receptors, wherein the composition comprises the tri-peptide KDI or a pharmaceutically acceptable salt thereof in combination with at least one pharmaceutically acceptable carrier, diluent or excipient.

Disorders responsive to the blockade of ionotropic glutamate receptors include a variety of central nervous system degenerative disorders, such as stroke, traumatic brain and spinal cord injury, Alzheimer's disease, Parkinson's disease, Huntington's chorea, amyotrophic lateral sclerosis (ALS) and spinal muscular atrophy (SMA).

Glutamate neurotoxicity (recently named as excitotoxicity) has been implicated in the pathophysiology of numerous neurological disorders. Besides the above-mentioned disorders, excitotoxicity has been linked with the etiology of cerebral deficits subsequent to cardiac bypass surgery and grafting, cerebral ischemia, spinal cord lesions resulting from inflammation, perinatal hypoxia, cardiac arrest, and hypoglycemic neuronal damage. In addition, excitotoxicity has also been implicated in such chronic neurodegenerative conditions as inherited ataxias, AIDS-induced dementia, as well as ocular damage and retinopathy. Other neurological disorders implicated with excitotoxicity and/or glutamate dysfunction include muscular spasticity including tremors, drug tolerance and withdrawal, brain edema, convulsive disorders including epilepsy, depression, anxiety and anxiety related disorders such as post-traumatic stress syndrome, tardive dyskinesia, and psychosis related to depression, schizophrenia, bipolar disorder, mania, and drug intoxication or addiction. In addition, it has also been reported that glutamate excitotoxicity participates in the etiology of acute and chronic pain states including severe pain, intractable pain, neuropathic pain, post-traumatic pain and also migraine.

The use of a biological neuroprotective agent, such as KDI or its salt, as a glutamate receptor antagonist, is likely to be safer and more usable in treating or preventing these disorders and/or reducing the amount of neurological damage associated with these disorders than drugs having often detrimental side effects.

Consequently, a further object of the present invention is a method of selectively inhibiting ionotropic glutamate receptors in a human host, comprising administering to a human host in need of such treatment a peptide compound that selectively inhibits activity of ionotropic glutamate receptors and comprises the tri-peptide KDI or a pharmaceutically acceptable salt thereof.

A very specific object of the invention is a method for treatment of stroke, comprising administering to a patient in need of such treatment a therapeutically effective amount of a pharmaceutical composition having an inhibitory effect on ionotropic glutamate receptors, wherein the composition comprises the tri-peptide KDI or a pharmaceutically acceptable salt thereof in combination with at least one pharmaceutically acceptable carrier, diluent or excipient.

ABBREVIATIONS

ALS Amyotrophic Lateral Sclerosis
AMPA α-amino-3-hydroxy-5-methyl-4-isoxazole-4-propionic acid
CNS Central Nervous System
KDI Lys-Asp-Ile
LRE Leu-Arg-Glu
NMDA N-methyl-D-aspartate
RT room temperature

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIGS. 1A and 1B.

1A: immunocytochemistry for AMPA (GluR1, GluR2/3, GluR4), and kainate (GluR5, GluR6/7, KA2) glutamate receptor subunits in human embryonic neocortical neurons. All cells are on poly-D-lysine at 14 days in vitro. Scale bar=20 µm.

1B: Immunocytochemistry for NMDA receptor subunits in human embryonic neocortical neurons. All cells are on poly-D-lysine at 14 days in vitro. Scale bar=20 µm.

FIGS. 2A and 2B.

2A: Example traces of 20 mM glutamate evoked currents in human neocortical neurons in the absence and presence of the KDI peptide (0.1-10 µg/ml). (n=15).

2B: A column presentation of percentages of inhibition of laminin-1 and its various derivatives on AMPA receptor currents of human neocortical neurons. Lam-1: laminin-1, P10-OH: an acidic form of RDIAEIIKDI, (n=5), P10-NH$_2$: an amide form of RDIAEIIKDI (n=5), P31: a control peptide from cell attachment domain of β1 laminin (CDPGYIGSR, n=6), and LRE: a control tri-peptide LRE from β2 laminin (n=5). Asterisks indicate statistical significance of inhibition between the control and the peptide treatment tested by t-test, $p<0.001$ (*), $p<0.01$ ().

FIGS. 3A, 3B and 3C.

Evaluation of KDI tri-peptide inhibition of AMPA currents of cultured human neocortical cells.

In 3A, an inhibition curve of increasing concentrations of the KDI peptide on AMPA currents evoked by 20 mM glutamate indicate an $IC_{50}$ of 0.1 µg/ml of the peptide (n=10). $P<0.001$ (***), $p<0.05$ (*).

In 3B, the glutamate dose-response curves indicate that 0.1 µg/ml of the KDI peptide does not essentially shift the $EC_{50}$, which indicates a non-competitive nature of inhibition (n=6).

In 3C, the significance of the length of KDI pre-application time for inhibition of AMPA receptor currents is demonstrated (n=6). The results show that the pre-application time is short (62±22 ms). In some experiments, a direct co-application of KDI and glutamate was tested. Under those conditions, the KDI peptide produced only a 37±20% inhibition of AMPA currents, which indicates that the KDI peptide directly interacts with the AMPA receptor.

FIGS. 4A and 4B.

In 4A, both individual traces and column presentation indicate that the pre-applied KDI peptide is a potent inhibitor of NMDA currents at 0.1-10 µg/ml (n=7). $p<0.001$ (***), $p<0.05$ (*).

In 4B, KDI inhibition of kainate receptor currents in HEK 293 cells transfected with GluR6 clones indicates almost 100% inhibition at 10 µg/ml ($p<0.001$ ***) of the KDI with an $IC_{50}$ at 0.1 µg/ml of the KDI peptide (n=6).

DETAILED DESCRIPTION OF THE INVENTION

To elucidate the possible interaction of the KDI-domain of γ1 laminin with the glutamate receptor function, we used immunocytochemistry and patch clamp configuration on human embryonic neocortical neurons cultured on a poly-D-lysine substratum. In addition, we applied patch clamp studies on HEK 293-cells expressing recombinant AMPA, and kainate receptor subunits. Immunocytochemically, neocortical neurons expressed all subclasses of glutamate receptors tested, but both expression patterns and subunit compositions showed considerable variation (FIGS. 1A-B).

Figure 1A:
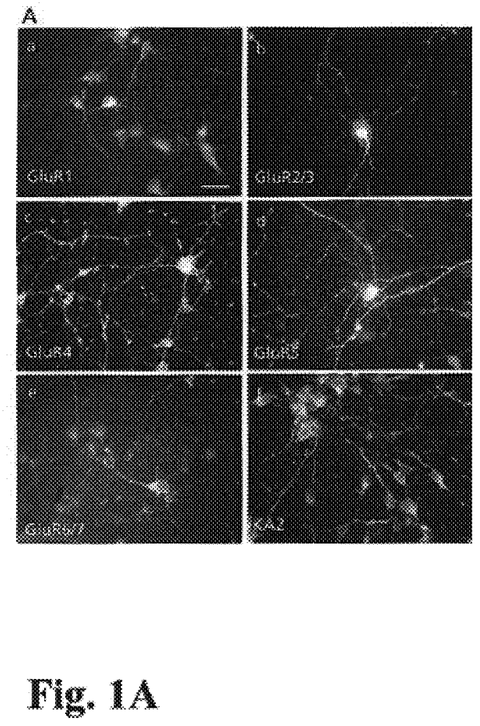

Consequently, in FIG. 1A immunocytochemistry for AMPA (GluR1, GluR2/3, GluR4), and kainate (GluR5, GluR6/7, KA2) glutamate receptor subunits in human embryonic neocortical neurons indicates that several different ionotropic glutamate receptor proteins are expressed, and their expression patterns show considerable variation. For example, the GluR1 receptor subunits are mainly expressed in cell bodies, while the GluR2/3 subunits are strongly and specifically expressed along the long neurites as well as cell bodies. Expression of GluR4 receptor subclass is moderate along both neurites and cell bodies. The GluR5 kainate subclass of glutamate receptors is clearly the prevailing subtype of all neocortical neurons being expressed as punctate deposits along the neurites. However, a weaker but distinct expression of the GluR6/7 kainate receptors is visualized along the mature-looking pyramidal neurons, and KA2 receptors are moderately expressed along both neurites and cell bodies of some of the neocortical neurons.

Figure 1B:
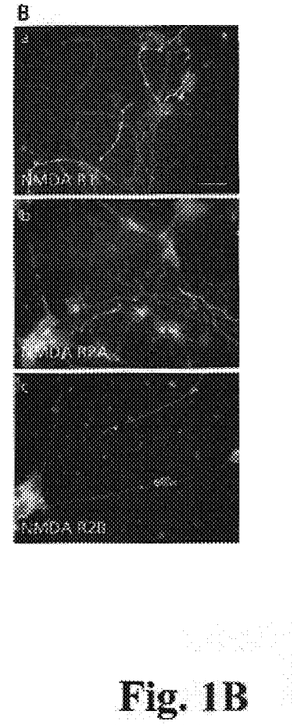

In FIG. 1B immunocytochemistry for NMDA receptor subunits in human embryonic neocortical neurons indicate that the NMDAR1 subunit is expressed in a patchy fashion along neurites of the neocortical neurons. Both NMDAR2A and NMDAR2B subunits show weak expression patterns mainly in the cell bodies of neurons. Thus, the neocortical neurons express at least the R1/R2A and R1/R2B heterodimeric receptor proteins.

Figure 2A:
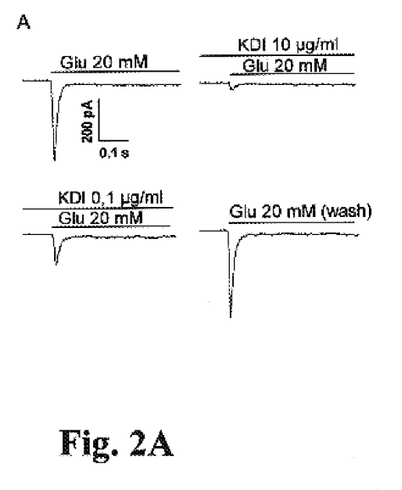

Application of glutamate to the cultured neocortical neurons under conditions that inhibit NMDA receptor currents, e.g., in the presence of 1.0 mM $Mg^{2+}$ in the external solution, produced a fast desensitizing current (FIG. 2A) that was effectively inhibited by 0.1-10 µg/ml of the KDI peptide (FIG. 2A). The glutamate-evoked current was solely AMPA receptor-mediated based on the fact that application of a selective kainate receptor agonist SYM 2081 together with 0.3 mg/ml of concanavalin A produced only a small (5 pA) insignificant current (data not shown). Thus, neocortical neurons on a poly-D-lysine substratum failed to express functional kainate receptors even though they showed expression of several kainate receptor subunit proteins (FIGS. 1A-B).

Figure 2B:
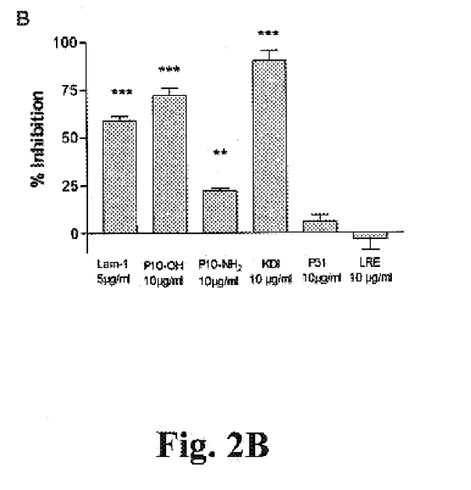
Figure 3A:
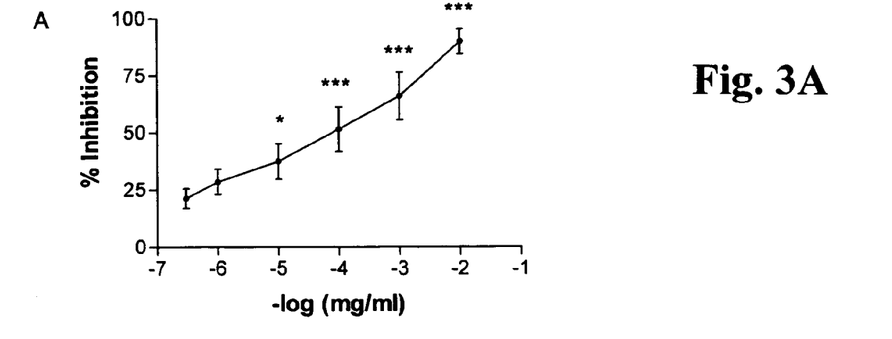

Laminin-1 and various peptide derivatives of the neurite outgrowth domain of γ1 laminin were found to inhibit AMPA receptor currents in cultured human neocortical neurons (FIG. 2B). Native laminin-1 (5 µg/ml=0.01 µM, α1β1γ1) inhibited currents evoked by 20 mM glutamate by 59±5% (FIG. 2B). Inhibition of a 10 amino acid long neurite outgrowth domain of γ1 laminin (RDIAEIIKDI) was dependent on the form of the synthesized amino acid chain. An acid (—OH) form of the peptide inhibited the AMPA receptor currents at the concentration of 10 µg/ml (10 µM) by 72±8% (FIG. 2B) whereas the amide (—$NH_2$) form only by 22±3% (FIG. 2B). The previously characterized shortest active domain of γ1 laminin, KDI, at a concentration of 10 µg/ml (30 µM) was also found active in inhibiting AMPA receptor currents by 90±13%, and at a concentration of 3 µg/ml (10 µM) by 75% (FIG. 3A). The cell attachment peptide CDPGYIGSR (P31) from the β1 laminin did not inhibit AMPA currents in a significant manner (FIG. 2B), and the previously identified active domain of the β2 laminin LRE was also inactive in modulating AMPA receptor currents of human neocortical neurons (FIG. 2B).

Example traces of 20 mM glutamate evoked currents in human neocortical neurons in the absence and presence of the KDI peptide (0.1-10 µg/ml) thus indicate that pre-application of KDI produces an inhibition, which is dose-dependent, washable and reproducible. A column presentation of FIG. 2B demonstrates a percentage of inhibition of laminin-1 and its various derivatives on AMPA receptor currents of human neocortical neurons. Laminin-1 (Lam-1), purified from mouse EHS-tumor (Martin and Timpl, 1987), produced a significant (*) inhibition of AMPA currents. P10-OH (RDIAEIIKDI-OH), an acid form of the neurite outgrowth domain of the γ1 laminin also produced effective (*) inhibition of AMPA receptors, whereas P10-$NH_2$, an amide form of the same, was much less efficient (). The KDI peptide was most efficient (*) in inhibiting AMPA currents, whereas a control peptide from cell attachment domain of β1 laminin (CDPGYIGSR), and a control tri-peptide LRE from β2 laminin did not affect AMPA receptor currents. Asterisks indicate statistical significance of inhibition between the control and the peptide treatment tested by t-test, $p<0.001$ (*), $p<0.01$ ().

Figure 3B:
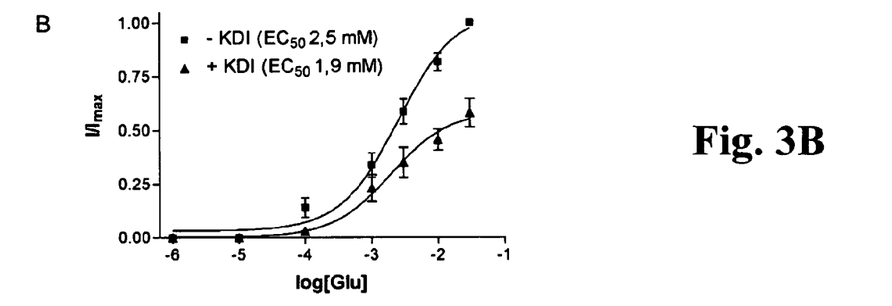
Figure 3C:
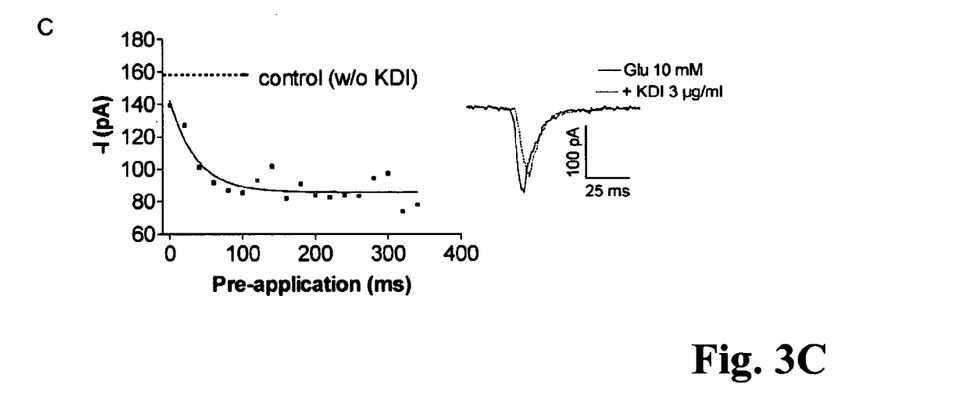

The acidic form of the KDI-peptide inhibited AMPA receptor currents of human neocortical neurons in a dose dependent manner, $IC_{50}$ being at 0.1 µg/ml (300 nM) of the tripeptide (FIG. 3A). Glutamate dose response curves were measured in the presence of 0.1 µg/ml of KDI (FIG. 3B). $EC_{50}$ values in the absence and presence of KDI were 2.5 and 1.9 mM, respectively, indicating a non-competitive inhibition of the receptor by the KDI peptide (FIG. 3B). The inhibitory effect of the KDI peptide on the AMPA receptor currents was a direct one. This was apparent from the fact that the KDI-induced inhibition required only a short pre-application of the peptide (62±22 ms) for maximal inhibition (FIG. 3C). Co-application of 3 µg/ml (10 µM) of the KDI with glutamate without KDI-pre-application produced an inhibition of only 37±20% (FIG. 3C), which was a minute one as compared to inhibition obtained with the KDI (3 µg/ml) pre-application (75%; see FIG. 2B).

Figure 4A:
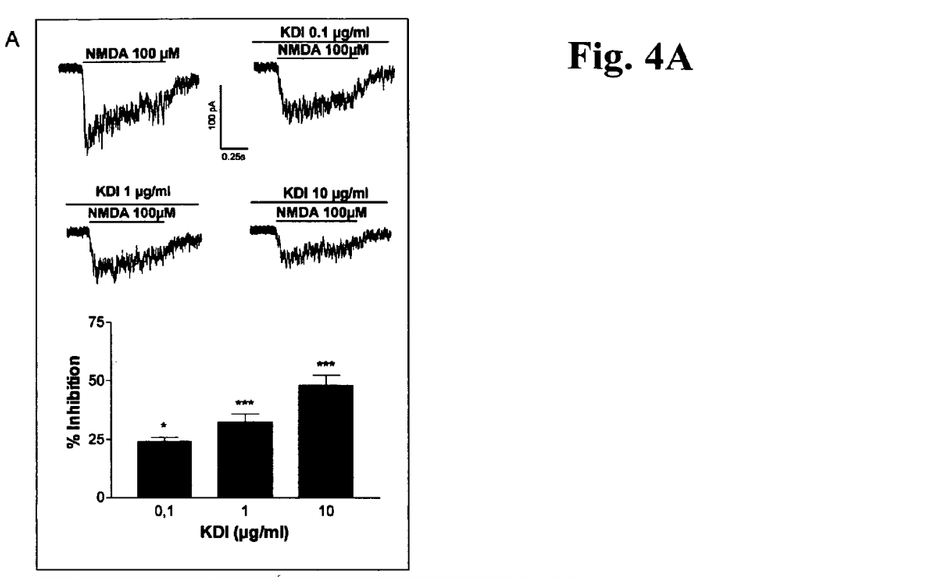

The effect of the KDI-peptide on NMDA receptor currents of human neocortical neurons was studied using 100 µM NMDA as an agonist, and an external solution without $Mg^{2+}$ (FIG. 4A). At 0.1-10 µg/ml (300 nM-30 µM), the KDI peptide produced an inhibition of 25-50% of the NMDA receptor currents (FIG. 4A).

Figure 4B:
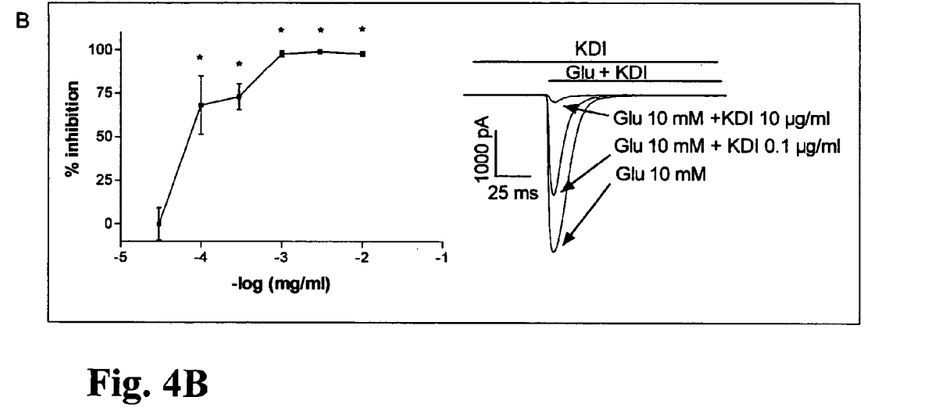

As we were unable to detect kainate receptor currents in human neocortical neurons even though they looked mature, healthy and expressed several kainate receptor subunits at the protein level (FIG. 1A), we used HEK 293 cells transfected with the GluR6 receptor subunit, also expressed by human cortical pyramidal neurons (FIG. 1A), to study the effects of the KDI-peptide on kainate receptor currents. Our results indicate that the GluR6 kainate receptors of the HEK 293 cells were equally sensitive to KDI-inhibition as the AMPA receptors of the human neocortical neurons showing an $IC_{50}$ at 0.1 µg/ml of KDI peptide (FIG. 4B). Recombinant AMPA receptors (GluR4 subtype) of the transfected HEK 293 cells, similar to human neocortical neurons (FIGS. 2-3), were highly sensitive to the inhibitory effect of KDI peptide. The KDI peptide at 10 µg/ml (30 µM) inhibited GluR4 currents evoked by 10 mM glutamate by 83±14%, $IC_{50}$ being approximately 0.1 µg/ml (data not shown).

In the present invention we thus show that laminin-1, and various peptide derivatives of the γ1 laminin, in particular the neurite outgrowth promoting KDI domain, inhibit AMPA receptor currents in human neocortical neurons in a dose-dependent and non-competitive manner. Similarly, the KDI-domain also inhibits NMDA receptor currents in neocortical neurons and recombinant kainate and AMPA receptor currents in transfected HEK 293-cells. The KDI peptide produces almost complete inhibition of AMPA and kainate receptors at 10 µg/ml (30 µM) and a 50% inhibition of the NMDA receptor currents. Thus, the KDI domain of γ1 laminin is a novel, extremely potent and universal antagonist of the major subclasses of ionotropic glutamate receptors.

The direct inhibition of glutamate receptor function by the KDI tri-peptide shown here reveals an entirely novel and biologically highly relevant function for the γ1 laminin and its KDI domain. Until now, the effects of extracellular matrix proteins, including the γ1 laminin, in the nervous system have been considered indirect and mediated via signalling cascades initiated by cell-matrix contacts.

That laminin-1 (composed of disulphide bonded α1β1γ1 laminins) and both the 10 amino acid neurite outgrowth domain (RDIAEIIKDI) of γ1 laminin, e.g., the amphiphilic peak of the γ1 laminin, and its shortest active KDI-domain all act as antagonists of AMPA-receptors indicate that the 10 amino acid neurite outgrowth domain, indeed, is facing the outside of the alpha-helical domain I of the C-terminus of laminin-1. That the acid form of the 10 amino acid peptide is far more efficient than its amide form and the acid form of the KDI domain is the most efficient antagonist of glutamate receptors indicate that these domains are likely to be cleaved by proteolysis from the laminin-1 molecule rather than being synthesized and secreted as naturally occurring peptides.

Never before has an extra-cellular matrix protein or its functionally active domain been shown to directly regulate the activity of a neurotransmitter activated ligand-gated ion channel. Even if previous studies have shown interaction between laminin and calcium and potassium channels, no electrical responses have been reported for this interaction. Thus, the present results are revolutionary in showing that the role of γ1 laminin in the CNS is not limited to promotion of neurite outgrowth, neuronal migration and regeneration with the assumption that all these functions are mediated solely by its adhesive properties. Even though the adhesive properties have been shown to play an important role in these biological events, the present data indicate that the neurite outgrowth KDI domain of γ1 laminin has additional diverse and important functions that shed new relevance for expression of γ1 laminin in adult CNS neurons, and in CNS after trauma or in a neurological disorder, such as Alzheimer's disease. The inhibitory function of the KDI domain on glutamate receptor function indicates that γ1 laminin may be expressed in adult neocortical and hippocampal neurons for protective and regulatory reasons essential for normal functioning of the CNS.

Recent studies from this laboratory offer the first practical examples on the regulatory and neuroprotective potential of the KDI domain in vivo. As compelling evidence indicates that glutamate neurotoxicity is a major player in all CNS trauma and neurodegenerative disorders, novel drugs used clinically to treat patients with Alzheimer's disease, ALS or stroke, are inhibitors of glutamate receptor function. In the present invention we show that the KDI tri-peptide is the only so far known universal inhibitor of ionotropic glutamate receptor function with already demonstrated ability to protect adult rat CNS against excitotoxicity. These results strongly imply that the KDI peptide may become one of the most efficient targeted medications for CNS trauma and disease.

The present invention thus provides natural, biologically active peptide compounds for medical use. The peptides are useful in soluble or substrate-bound forms in the treatment of disorders responsive to the blockade of ionotropic glutamate receptors. Consequently, the KDI peptide can be used in treating neurodegenerative diseases, such as Parkinson's or Alzheimer's disease, ALS or stroke. A suitable pharmaceutical composition for that purpose is an injectable liquid to be administered to the intrathecal space or injected to the brain tissue.

The peptides of the present invention may be prepared using conventional methods for peptide synthesis, as described, for instance, by Liesi et al. (1989).

The term "pharmaceutically acceptable salt" as used herein, refers to salts of the peptides employed in the present invention which are substantially non-toxic to living organisms. Typical pharmaceutically acceptable salts include salts prepared by reaction of the peptide compounds of the present invention with a pharmaceutically acceptable mineral or organic acid or an organic or inorganic base. Such salts are known as acid addition and base addition salts.

The peptide compounds employed in the methods of this invention may also occur in any other pharmaceutically acceptable form which a peptide compound may take by a reaction characteristic of the functional groups of such a peptide compound.

The term "pharmaceutically acceptable carriers, diluents and excipients" as used herein refers to vehicles or additives conventionally used in formulating pharmaceutical compositions.

Pharmaceutical compositions containing the peptides of the invention for the treatment of neurodegenerative diseases are preferably liquid preparations suitable for injection. The peptides may be dissolved in sterile saline or water. A pharmaceutical composition may include a modification of the KDI peptide that allows its direct access to the CNS through the blood-brain-barrier, and also include biodegradable polymers, which slowly release the peptide and simultaneously, as an additional advantage, provide a direction for the growing axons.

The peptides of the present invention may thus be administered in a therapeutically effective amount within a wide dosage range. The therapeutically effective amount depends on the age and condition of the tissue in question. Peptides of the present invention may be administered either as a single dose, or as continuous administration using, for instance, a mini pump system. In the latter case, the daily dosage will not exceed the dose of a single injection, and must be pre-determined by animal experimentation.

The concentrations of a peptide of the invention in a pharmaceutical composition are generally between 0.01 and 100 μg/ml. However, it should be noted that the optimal concentration of the KDI peptide may be domain dependent or tissue dependent, and therefore pre-testing of the dosage is of utmost importance. Determining of the suitable dosage for individual treatments is within the skills of those familiar with the art.

The pharmaceutical composition of the present invention can be administered by any means that achieve the intended purpose. For instance, for the treatment of stroke the composition can be administered to the injury site via a catheter, or intravenously. In Alzheimer's disease and Parkinson's disease the pharmaceutical composition of the present invention may be continuously administered by using local application via a catheter or patch, or systemically via intravenous infusion or a pill, provided that KDI or any of its pharmaceutically acceptable form can be orally administered and will cross blood-brain-barrier.

In spinal cord trauma or injury a most preferable way of administration is using a mini pump system to administer the peptide composition directly to the trauma area of the spinal cord. This can be easily carried out in connection with orthopaedic surgery for disclosing the trauma area.

In ALS, the administration may be carried out directly into the cerebrospinal fluid at the lumbar level via a mini pump or patch or, alternatively, orally or intravenously.

The pharmaceutical compositions of the present invention can be administered to any animal that can experience the beneficial effects of the peptides of the invention. Human beings are foremost among such animals, although the invention is not intended to be limited to the medical treatment of human beings.

An advantageous feature of the KDI peptide is the fact that it is a short peptide, being not immunogenic, and therefore risks for immunological reactions are minimal. Furthermore, as the peptide has previously been disclosed as a flavoring ingredient, it should be safe for human use.

EXPERIMENTAL

Human CNS-Tissues

Human fetal CNS-tissues were obtained from 8-11 week old fetuses after legal abortion, and after informed consent from the patients. The tissues were collected within 2-4 hrs by the permission of the Ethics Committee of the Maternity Hospital of the Central University Hospital.

Neuronal Cultures

The CNS tissues were first placed in cold saline. The neocortical areas of 11-week embryos were identified under a stereomicroscope, and carefully freed of meningeal membranes. Neuronal cultures were prepared as described previously (Liesi et al., 2001) and plated at $2 \times 10^4$ on glass coverslips pre-coated with poly-D-lysine (10 mg/ml, Collaborative Research) in Neurobasal medium (Gibco, U.K.) with B27-supplement (Gibco, U.K.), antibiotics and 500 µM L-glutamine. After 14-30 days in culture, the cultures were fixed in 2% paraformaldehyde/PBS pH 7.4 for 15 min at room temperature (RT), and processed for immunocytochemistry.

Analysis of Glutamate Receptors in Cultured Human Neocortical Neurons

Highly specific rabbit polyclonal antibodies (Upstate, N.Y., USA) against AMPA, kainate and NMDA receptor subunits were used at 5-10 µg/ml. After fixation, the cultures were treated in 0.05% Tween-20 in PBS pH 7.4 for 30 min at RT, washed in PBS and incubated with polyclonal anti-glutamate receptor antibodies diluted in PBS for 1 hr at RT. After a brief wash in PBS, the cultures were incubated with anti-rabbit immunoglobulins coupled to FITC for 30 min at RT, washed once in PBS and mounted in PBS:Glycerol (1:1). The cultures were viewed using an Olympus BX51 microscope with appropriate filters and photographed using an Olympus DP70 digital camera.

Electrophysiology of Human Neocortical Neurons and HEK 293 Cells

For whole cell patch clamp recordings, cultures were placed under an inverted microscope (Olympus IX71). During recordings neurons were continuously superfused with an external solution (pH 7.4) containing in mM: 150 NaCl, 2.5 KCl, 2.5 $CaCl_2$, 1 $MgCl_2$, 10 HEPES, and 10 glucose. Experiments were carried out at room temperature. Patch clamp pipettes had a resistance of 4 to 7 MΩ when filled with an internal solution containing in mM: 100 N-methyl-D-glucamine, 100 $CH_3SO_3H$, 40 CsF, 10 $MgCl_2$, 10 HEPES, and 5 EGTA, pH adjusted with CsOH to 7.4. Cells were clamped at a holding potential of −60 mV. Drugs were diluted in external solution and applied to cells with a multi-barrel fast solution application system (Warner Instrument, Hamden, Conn.). In most experiments, the test-drugs (e.g., laminin-1 and various laminin peptides) were first pre-applied to cells followed by co-application of the agonist and the test-drug. Currents were recorded using Axopatch 200B amplifier and pClamp 8.0 software (Axon Instruments, Inc., Foster City, Calif.) and stored to the hard drive of PC computer. Recordings were sampled at 20 Hz and filtered with 1 Kz lowpass bessel filter. Data were analyzed with pClamp8.0 software. Statistical analysis of results was done with the Prism 3.02 software (Graphpad, San Diego, Calif.) using a repeated Measures ANOVA and Dunnett's post-test. L-glutamate and concanavalin A were from Sigma (St. Louis, Mo.) and SYM 2081 and NMDA were from Tocris (Avonmouth, UK). Mouse native laminin-1 was from Boehringer-Mannheim (Germany). All synthetic peptides were from Multiple Peptide Systems (San Diego, Calif.).

Human embryonic kidney cells (HEK 293 cells) were cultured in Dulbecco's modified Eagle's medium supplemented with 10% fetal calf serum and 2 mM L-glutamine and 1% penicillin-streptomycin solution. Cells were transfected with recombinant GluR4 (AMPA) and GluR6 (kainate) receptor subunit cDNA-clones using calcium phosphate method as previously described (Pasternack et al., 2002).

REFERENCES

Guadagno, E. and Moukhles, H. Laminin-induced aggregation of the inwardly rectifying potassium channel, Kir4.1, and the water-permeable channel, AQP4, via a dystroglycan-containing complex in astrocytes. Glia 47:138 (2004).

Liebkind, R., Laatikainen, T. and Liesi, P. Is the soluble KDI domain of gamma-1 laminin a regeneration factor for the mammalian central nervous system? J. Neuroscience Res. 73:637 (2003).

Liesi, P., Närvänen, A., Soos, J., Sariola, H. and Snounou, G. Identification of a neurite outgrowth promoting domain of laminin using synthetic peptides. FEBS Lett. 244:141 (1989).

Liesi, P. Extracellular matrix and neuronal movement. Experientia 46:900 (1990).

Liesi, P., Fried, G. and Stewart, R. Neurons and glial cells of the embryonic human brain and spinal cord express multiple and distinct isoforms of laminin. J. Neuroscience Res. 64: 144 (2001a).

Liesi, P., Laatikainen, T. and Wright, J. M. A biologically active sequence (KDI) mediates the neurite outgrowth function of the gamma-1 chain of laminin-1. J. Neuroscience Res. 66:1046 (2001b).

Liesi, P. and Kauppila, T. Induction of type IV collagen and other basement membrane associated proteins after spinal cord injury of the adult rat may participate in formation of the glial scar. Exp. Neurol. 173:31 (2002).

Martin, G. R. and Timpl, R. Laminin and other Basement Membrane Components. Annual Review of Cell Biology 3:57 (1987).

Mattson, M. P. Excitotoxic and excitoprotective mechanisms: abundant targets for the prevention and treatment of neurodegenerative disorders. Neuromolecular Med. 3:65 (2003).

Meiners, S. and Mercado, M. L. Functional peptide sequences derived from extracellular matrix glycoproteins and their receptors: strategies to improve neuronal regeneration. Mol. Neurobiol. 27:177 (2003).

Miner, J. H. and Yurchenco, P. D. Laminin functions in tissue morphogenesis. Annu. Rev. Cell Dev. Biol. 20:255 (2004).

Murtomäki, S., Risteli, L., Risteli, J., Johansson, S., Koivisto, U-M. and Liesi, P. Laminin and its neurite outgrowth promoting domain associate with the Alzheimer's and Down's syndrome brains. J. Neuroscience Res. 32:261 (1992).

Nishimune, H., Sanes, J. R. and Carlson, S. S. A synaptic laminin-calcium channel interaction organizes active zones in motor nerve terminals. Nature 432:580 (2004).

Palu, E. and Liesi, P. Differential distribution of laminins in Alzheimer's and normal brain tissues. J. Neuroscience Res. 69:243 (2002).

Pasternack, A., Coleman, S. K., Jouppila, A., Mottershead, D. G., Lindfors, M., Pasternack, M. and Keinänen, K. Alpha-amino-3-hydroxy-5-methyl-4-isoxazolepropionic acid (AMPA) receptor channels lacking the N-terminal domain. J. Biol. Chem. 277:49662 (2002).

Wiksten, M., Liebkind, R., Laatikainen, T. and Liesi, P. γ1 laminin and its biologically active KDI-domain may guide axons in the floor plate of the embryonic human spinal cord. J. Neuroscience Res. 71:338 (2003).

Wiksten, M., Väänänen, A. J., Liebkind, R. and Liesi, P. Regeneration of adult spinal cord is promoted by the soluble KDI-domain of γ1 laminin. J. Neuroscience Res. 78:403 (2004a).

Wiksten, M., Väänänen, A. J., Liebkind, R., Rauhala, P. and Liesi, P. The soluble KDI-domain of γ1 laminin protects adult rat hippocampus from excitotoxicity of kainic acid. J. Neuroscience Res. 78:411 (2004b).

inhibitory effect on ionotropic glutamate receptors, wherein the composition consists of the tri-peptide KDI or a pharmaceutically acceptable salt thereof, in combination with one or more of a pharmaceutically acceptable carrier, diluent or excipient.

4. A method for treatment of a neurological disorder or neurodegenerative disease selected from the group consisting of Alzheimer's disease, Parkinson's disease, amyotrophic lateral sclerosis (ALS), and spinal cord injury, comprising administering to a patient in need of such treatment a therapeutically effective amount of a composition having an inhibitory effect on ionotropic glutamate receptors, wherein the composition consists of the tri-peptide KDI or a pharma-

The invention claimed is:

1. A method for antagonizing the neurotoxicity mediated by ionotropic glutamate receptors, said method comprising administering to a patient in need of such antagonizing a therapeutically effective amount of a sterile pharmaceutical composition having inhibitory effect on ionotropic glutamate receptors, wherein the composition consists of the tri-peptide KDI or a pharmaceutically acceptable salt thereof in combination with one or more of a pharmaceutically acceptable carrier, diluent or excipient.

2. A method of selectively inhibiting ionotropic glutamate receptors in a human host, comprising administering to a human host in need of such treatment a peptide compound derived from the γ1-chain of laminin-1 that selectively inhibits activity of ionotropic glutamate receptors, wherein the peptide compound consists of the tripeptide KDI or a pharmaceutically acceptable salt thereof dissolved in sterile saline or water.

3. A method for treatment of stroke, comprising administering to a patient in need of such treatment a therapeutically effective amount of a pharmaceutical composition having an inhibitory effect on ionotropic glutamate receptors, wherein the composition consists of the tri-peptide KDI or a pharmaceutically acceptable salt thereof, in combination with one or more of a pharmaceutically acceptable carrier, diluent or excipient.

5. The method according to claim 4, wherein the neurodegenerative disease is Parkinson's disease.

6. The method according to claim 4, wherein the neurodegenerative disease is Alzheimer's disease.

7. The method according to claim 4, wherein the neurodegenerative disease is amyotrophic lateral sclerosis (ALS).

8. The method according to claim 4, wherein the neurological disorder is spinal cord injury.

9. A method for treatment of a neurological disorder or neurodegenerative disease selected from the group consisting of Alzheimer's disease, Parkinson's disease, amyotrophic lateral sclerosis (ALS), spinal cord injury, and stroke, the disorder or disease being responsive to the blockade of ionotropic glutamate receptors, comprising administering to a patient in need of such treatment a therapeutically effective amount of a composition having an inhibitory effect on ionotropic glutamate receptors, wherein the composition consists of the tri-peptide KDI or a pharmaceutically acceptable salt thereof, in combination with one or more of a pharmaceutically acceptable carrier, diluent or excipient.

10. The method according to claim 9, wherein the neurodegenerative disease is Parkinson's disease.

11. The method according to claim 9, wherein the neurodegenerative disease is Alzheimer's disease.

12. The method according to claim 9, wherein the neurodegenerative disease is amyotrophic lateral sclerosis (ALS).

13. The method according to claim 9, wherein the neurological disorder is spinal cord injury.

14. The method according to claim 9, wherein the neurological disorder is stroke.

* * * * *

```
                               SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence:  Synthetic
      decapeptide derived from the neurite outgrowth-promoting domain of
      laminin-1

<400> SEQUENCE: 1

Arg Asp Ile Ala Glu Ile Ile Lys Asp Ile
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:  Synthetic
      peptide derived from the neurite outgrowth-promoting domain of
      laminin-1

<400> SEQUENCE: 2

Glu Ile Ile Lys Asp Ile
1               5
```